United States Patent
Nolte et al.

(10) Patent No.: US 9,723,989 B2
(45) Date of Patent: Aug. 8, 2017

(54) EX VIVO MOTILITY CONTRAST IMAGING

(71) Applicant: Purdue Research Foundation, West Lafayette, IN (US)

(72) Inventors: David D. Nolte, Lafayette, IN (US); John J. Turek, West Lafayette, IN (US); Ran An, West Lafayette, IN (US)

(\*) Notice: Subject to any disclaimer, the term of this patent is extended or adjusted under 35 U.S.C. 154(b) by 0 days.

(21) Appl. No.: 15/000,773

(22) Filed: Jan. 19, 2016

(65) Prior Publication Data
US 2016/0210748 A1 Jul. 21, 2016

Related U.S. Application Data

(60) Provisional application No. 62/104,899, filed on Jan. 19, 2015.

(51) Int. Cl.
*G06K 9/00* (2006.01)
*A61B 5/00* (2006.01)
(Continued)

(52) U.S. Cl.
CPC ........ *A61B 5/0066* (2013.01); *G01B 9/02087* (2013.01); *G01B 9/02091* (2013.01); *G01N 21/4795* (2013.01); *G02B 21/14* (2013.01); *G02B 21/365* (2013.01); *G06T 7/0012* (2013.01); *G06T 2207/30024* (2013.01)

(58) Field of Classification Search
CPC ......... G06T 7/0012; G06T 2207/10101; G06T 2207/30024; A61B 5/0066; G01B 9/02087; G01B 9/02091; G01N 21/4795; G02B 21/14; G02B 21/365
See application file for complete search history.

(56) References Cited

U.S. PATENT DOCUMENTS 8,337,387 B2 \* 12/2012 Wong .................. C12N 5/0604
600/33
8,886,295 B2 \* 11/2014 Nolte .................. G03H 1/0443
356/450

(Continued)

OTHER PUBLICATIONS

Nolte, David D. "Biodynamic Imaging: Rethinking Cancer Care using Light-Scattering Theranostics." Biomedical Optics. Optical Society of America, 2014.\*

(Continued)

*Primary Examiner* — Jonathan S Lee
(74) *Attorney, Agent, or Firm* — Bose McKinney & Evans LLP

(57) ABSTRACT

In a method for ex vivo evaluation of tissue response, a target biological sample is placed in a chamber of a sample holder. Biodynamic imaging (BDI) is performed on the sample to extract BDI data of the entire sample, optical coherence imaging (OCI) data is generated from the BDI data; and then motility contrast imaging (MCI) data is generated from the OCI data. The MCI data is used to select an area of the ex vivo sample having the highest normalized standard deviation (NSD) value, indicative of a region of desirable responsiveness to a stimuli. The sample is subjected to a perturbation or external condition and an MCI analysis is performed on the selected area to determine the tissue response to the perturbation or external condition. In one aspect, the selected area or region of interest is obtained using a gradient descent method.

7 Claims, 15 Drawing Sheets

(51) Int. Cl.
    *G01B 9/02*     (2006.01)
    *G01N 21/47*    (2006.01)
    *G06T 7/00*     (2017.01)
    *G02B 21/14*    (2006.01)
    *G02B 21/36*    (2006.01)

(56) References Cited

U.S. PATENT DOCUMENTS

2010/0331672 A1* 12/2010 Nolte ............... G03H 1/0443
                                                      600/425
2015/0079621 A1*  3/2015 An .................. G01N 15/1434
                                                      435/29
2015/0124259 A1*  5/2015 An ................... A61B 5/0073
                                                      356/456
2015/0127309 A1*  5/2015 Am ................... G06F 19/24
                                                      703/2

OTHER PUBLICATIONS

Nolte, David D., et al. "Biodynamic 3D imaging for personalized cancer care." CLEO: Applications and Technology. Optical Society of America, 2014.*

Sun, Hao, et al. "Biodynamic profiling of three-dimensional tissue growth techniques." SPIE BiOS. International Society for Optics and Photonics, 2016.Merrill, Daniel A., et al. "Role of cellular adhesions in tissue dynamics spectroscopy." SPIE BiOS. International Society for Optics and Photonics, 2014.*

Merrill, Daniel A., et al. "Role of cellular adhesions in tissue dynamics spectroscopy." SPIE BiOS. International Society for Optics and Photonics, 2014.*

An, Ran, et al., "Phenotypic Profilinlg of Raf Inhibitors and Mitochondrial Toxicity in 3D Tissue Using Biodynamic Imaging," Journal of Biomolecular Screening, Dec. 20, 2013 (13 pages).

* cited by examiner

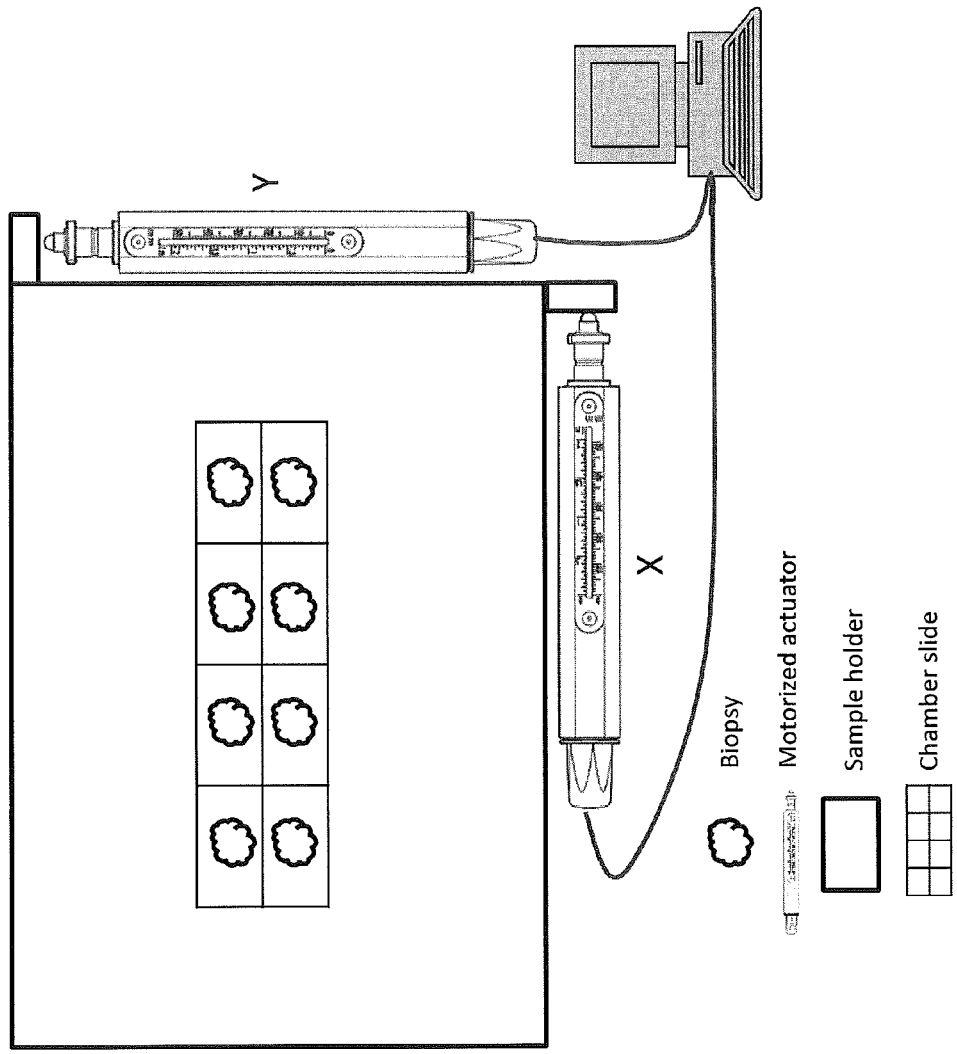

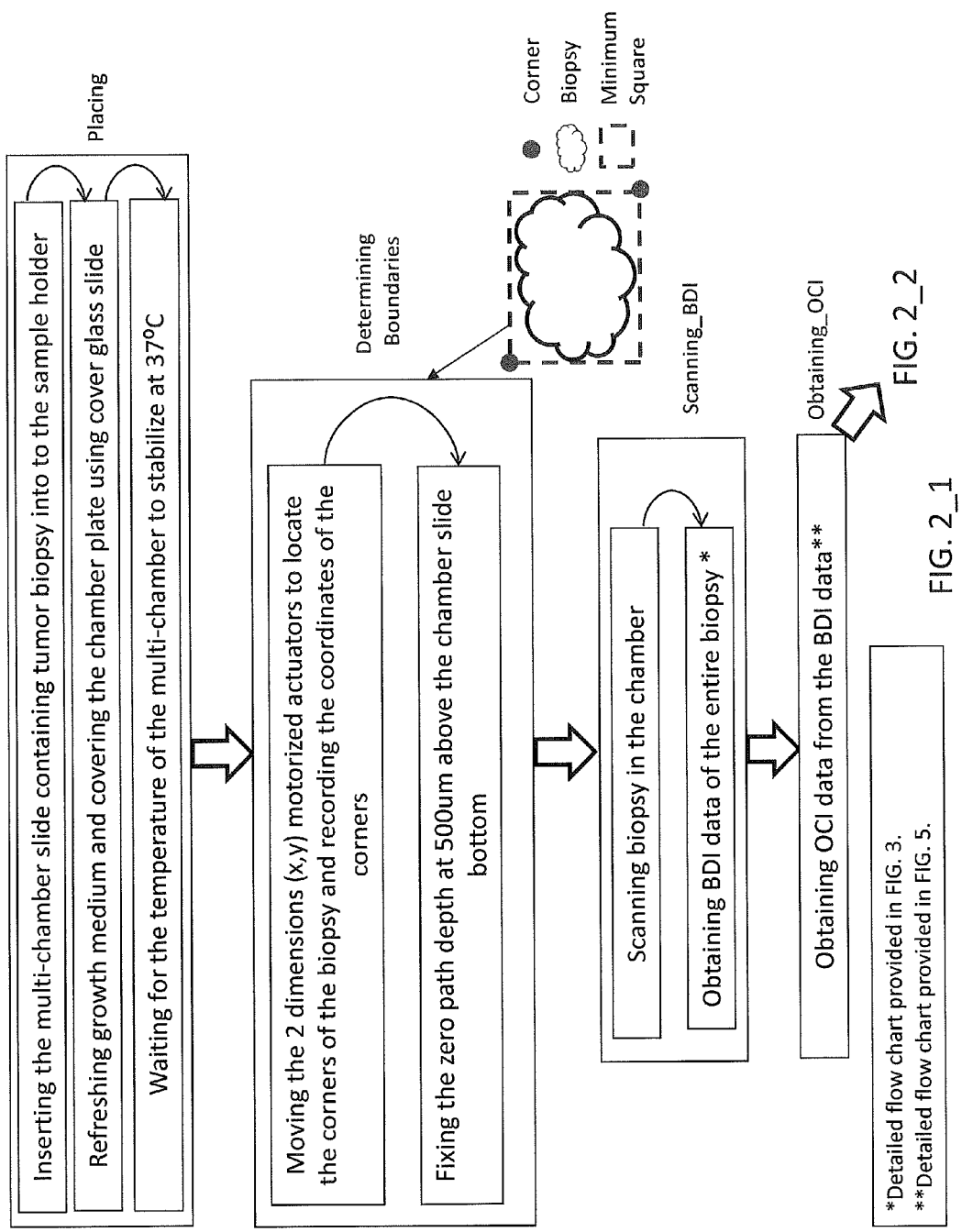

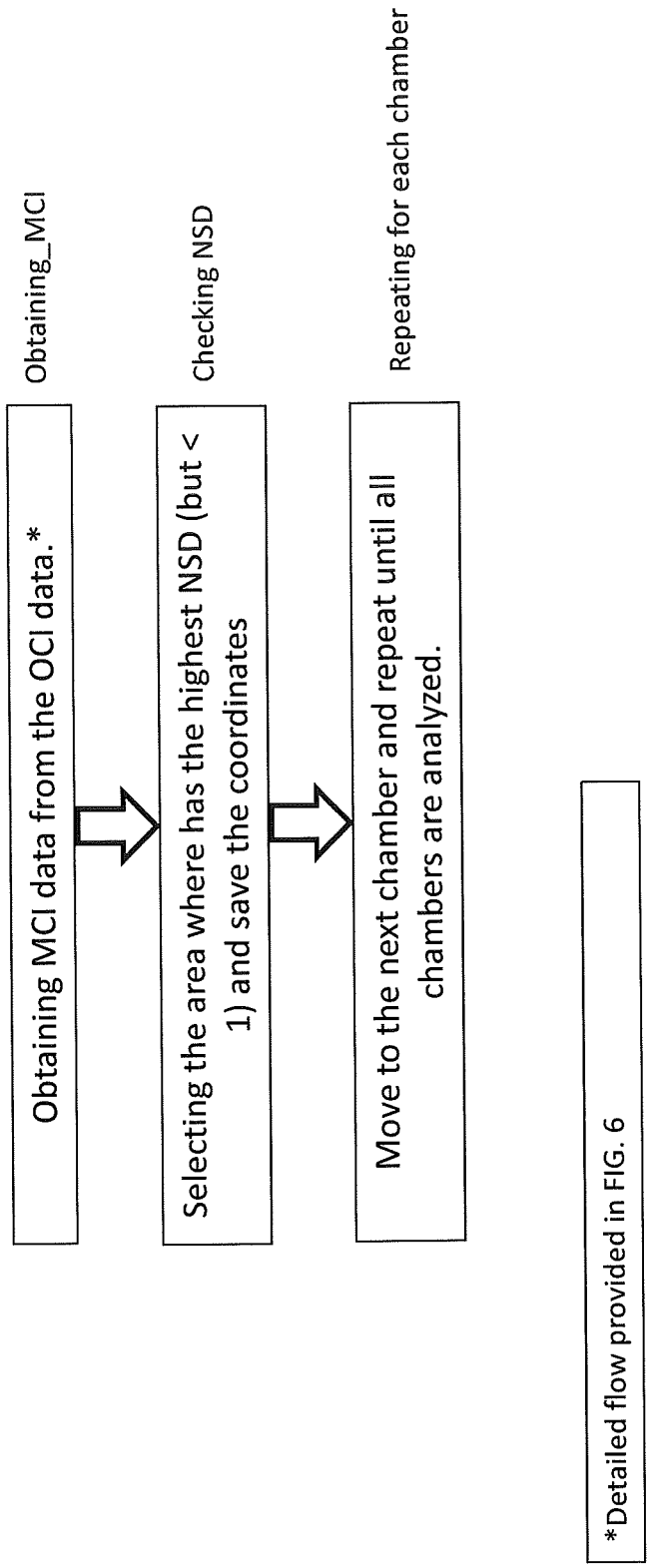
FIG. 2_2

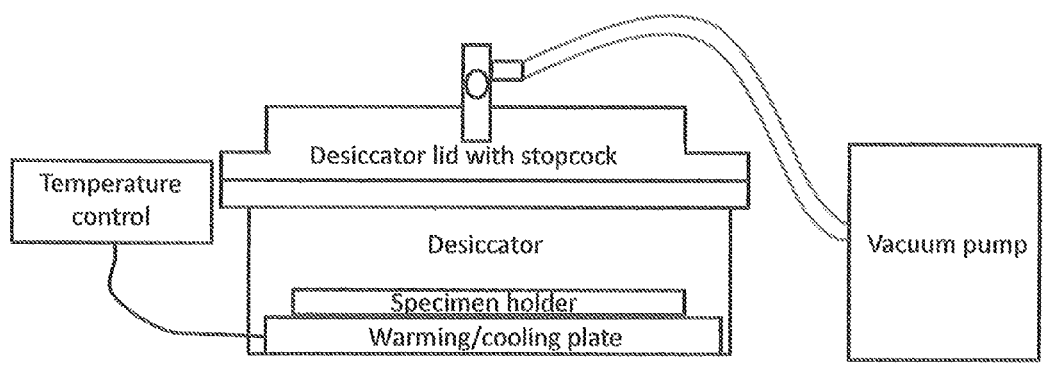
FIG. 8
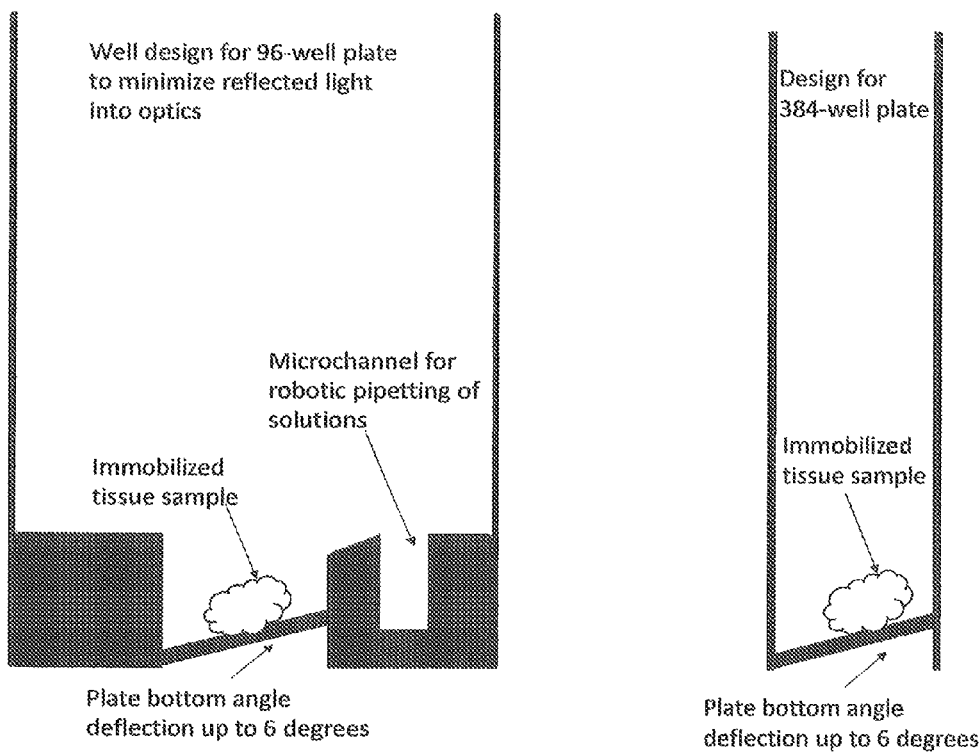
FIG. 9A
FIG. 9B

MCS characteristic metric 3.2 ──────────────────────────────→ 13

| A) Place MCS in non-coated tissue culture assay plate and allow to attach for 24 hours to immobilize | B) Place MCS in coated[1] tissue culture assay plate and allow to attach for 4-6 hours to immobilize.<br><br>[1]tissue culture assay plate coated with serum or 1% gelatin by incubation at 37C for 4 hours and then removing an drying of sample wells | C) Place MCS in non-coated tissue culture assay plate and embedded MCS in 0.5-1% low-gel temperature agarose containing base tissue culture medium for cell line |
|---|---|---|

FIG. 16

EX VIVO MOTILITY CONTRAST IMAGING

PRIORITY CLAIM AND REFERENCE TO RELATED APPLICATION

This application is a utility filing from and claims priority to provisional application Ser. No. 62/104,899, filed on Jan. 19, 2015, the entire disclosure of which is incorporated herein by reference.

STATEMENT OF GOVERNMENT INTEREST

This invention was made with government support under CBET-0756005 awarded by the National Science Foundation and EBO16582 awarded by the National Institutes of Health. The government has certain rights in the invention.

TECHNICAL FIELD

The present disclosure generally relates to tissue imagery, and in particular to ex vivo motility contrast imaging.

BACKGROUND

Live cell imaging has become the standard for high-content analysis and drug discovery applications. The most common assays on live cells include viability, proliferation and cytotoxicity assays as cellular physiology and function are measured while responding to applied perturbations. Cellular and tissue viability assays are typically measured using exogenous vital dyes as biomarkers of membrane integrity and cellular metabolic activity. However, these techniques are invasive and potentially toxic, and often require fixing of the tissue or permeabilization of the membranes. Furthermore, the common format of high-content analysis and flow cytometry requires isolated cells, or cells distributed on flat hard surfaces.

The need to perform viability, cytotoxicity and proliferation assays in three-dimensional (3D) tissue has become increasingly urgent, primarily because drug response in two dimensions (2D) is often not the same as drug response in biologically-relevant three dimensional culture. This is in part because genomic profiles are not preserved in primary monolayer cultures. There have been several studies that have tracked the expression of genes associated with cell survival, proliferation, differentiation and resistance to therapy that are expressed differently in 2D cultures relative to three-dimensional culture. For example, three-dimensional culture from cell lines of epithelial ovarian cancer, hepatocellular carcinoma or colon cancer display expression profiles more like those from tumor tissues than when grown in 2D. In addition, the three-dimensional environment of 3D culture presents different pharmacokinetics than 2D monolayer culture and produce differences in cancer drug sensitivities.

Multicellular resistance (MCR) is a process that occurs only in groups of cells or inside solid tumors. Standard two-dimensional chemosensitivity/resistance assays (CSRAs) have failed to measure the occurrence of MCR because monolayer cultures lack the natural morphology and cellular microenvironments of normal tissues. The present disclosure contemplates a new class of predictive screen that is fundamentally different than CSRAs because it uses 3D living-tissue rather than isolated cells. Cells thrive in three-dimensional environments and communicate with near and distant neighbors. It is now known that cells in 2D do not behave as cells do in 3D tissues, with different genetic expression profiles, different intercellular signaling, and different forces attaching them to their environment. Therefore, understanding relevant biological functions requires the capture of dynamical processes and motions in three dimensions.

There are many physiological and tumor micro-environmental causes of MCR. For instance, drugs can be chemically inactivated by the chemical environment inside the tissue. The low oxygen and nutrient concentrations inside tissue induce cellular quiescence in which cells exit the cell cycle and are no longer influenced by anti-proliferative cancer drugs, and hence require pro-apoptotic drugs that remain active in the hypoxic microenvironment. Chronic hypoxia inside avascular tumors selects for cellular phenotypes that have the ability to differentiate into multiple cell types. In addition, the hypoxic microenvironment induces the expression of hypoxia-inducible factor HIF-1α that participates in complex intracellular signaling cascades that cause cell cycle arrest or apoptosis, but also can promote cell survival as well as the epithelial-to-mesenchymal transition (EMT). It is notable that hypoxia plays at least some role in all of these causes of MCR and has become a major focus of current cancer research, both in terms of evolution of metastatic virulence and therapeutics.

A barrier to progress has been the lack of a 3D biologically functional assay that is able to extract information from inside tissue far from surfaces. Biodynamic imaging (BDI) provides the required depth capability, the sensitivity to cellular motions, and the signatures of different dynamical cellular functions. The present disclosure relies on these advantages of BDI to provide a 3D-tissue label-free therapeutic efficacy assay. The multicellular spheroid model is relevant for multicellular resistance (MCR) studies because tumor spheroids are very similar to avascular tumors with heterogeneous hypoxic internal environments characterized by anaerobic glycolysis, acidosis and necrosis. This heterogeneous and hostile internal tumor microenvironment is an incubator for multicellular resistance.

Biodynamic imaging (BDI) is a novel functional imaging approach that penetrates up to 1 mm inside tissue to extract the subcellular motions that define the dynamics and functional responses of living tissues to anti-cancer drugs. It is label-free and non-invasive. The cellular function accessed by tissue-dynamics imaging is not a surrogate monitor of tissue responding to stimuli, but is the actual functioning behavior of the living system. BDI can time-resolve (within 100 msec) changes in these motions as tissues evolve under environmental or pharmacological perturbations. These include organelles transported by ATP-driven molecular motors, actin-myosin-driven membrane undulations, cytoplasmic streaming, telophase and cytokinesis, apoptosis and necrosis, among others. BDI produces unique fingerprints of the action of specific drugs on the motion in specific cell lines. These drug fingerprints give insight into drug mechanisms of action and provide the training set for phenotypic profiling for the classification and discovery of potentially new drugs or new mechanisms of action.

One form of biodynamic imaging it tissue dynamics spectroscopic imaging which is a method that operates on data obtained from holographic optical coherence imaging (OCI). OCI is an optical signal acquisition and processing method which provides three-dimensional images from within an optical scattering medium, e.g., biological tissue. The holographic capture of depth-resolved images from optically thick living tissues has developed through several stages. Optical coherence imaging uses coherence-gated holography to optically section tissue up to 1 mm deep. It is a full-frame imaging approach, closely related to en face optical coherence tomography, but with deeper penetration and high-contrast speckle because of the simultaneous illumination of a broad area. The first implementations of OCI used dynamic holographic media such as photorefractive quantum wells to capture the coherent backscatter and separate it from the high diffuse background.

Digital holography approaches have replaced the dynamic media and have become the mainstay of current implementations of OCI. Highly dynamic speckle was observed in OCI of living tissues caused by dynamic light scattering from the intracellular motions. The dynamic speckle was used directly as an endogenous imaging contrast in motility contrast imaging (MCI) that could track the effects of antimitotic drugs on tissue health.

MCI captures the overall motion inside tissue, but is limited to imaging contrast. The OCI data includes dynamic speckle that is localized from a specified depth within the biological specimen up to 1 mm deep. The technique for isolating dynamic speckle is known including a method for converting the dynamic speckle into time-frequency spectrograms that can be interpreted in terms of biological function and can be applied to phenotypic profiling of drug candidates.

While there has been a considerable amount of improvement of in vitro tissue interrogation through OCI and MCI, there is still an unmet need for an ex vivo imaging arrangement. On difficulty presented by ex vivo imaging is that the optics of the tissue are different than for in vitro tissue. For instance, ex vivo tissue can include blood which can compromise the OCI and MCI imaging.

SUMMARY

A method for ex vivo evaluation of tissue viability comprises obtaining a sample of a target tissue and placing the sample in a chamber of a sample holder; performing biodynamic imaging (BDI) on the sample to extract BDI data of the entire sample; generating optical coherence imaging (OCI) data from the BDI data; and then generating motility contrast imaging (MCI) data from the OCI data. The method further contemplates using the MCI data to select an area of the ex vivo sample having the highest normalized standard deviation (NSD) value. The sample is subjected to a perturbation or external condition and an MCI analysis is performed on the selected area to determine the tissue response to the perturbation or external condition.

The present disclosure contemplates a non-parametric maximum likelihood apparatus and method for identifying regions of a biological sample to be evaluated to assess or predict response therapy. The disclosed method relies on a gradient descent or ascent in drug-response spectrogram space. A drug response spectrogram is generated and then a semi-local scalar field is generated based on spectrograms from a limited area or region of interest (ROI) of the biological sample. A spatial gradient operator is constructed that points in the direction of maximum ascent/descent from the current ROI. The gradient information is provided to a motion control system to step the imaging device by one ROI radius (or diameter) in the direction of the unit gradient vector. Another semi-local set of spectrograms is constructed at this new ROI, a new gradient vector is constructed, and the process is iterated. The process continues until a stationary region of the scalar field is reached. This stationary region is identified as the primary ROI for particular biological sample to evaluate or predict the response to the overall biological sample to a particular stimuli or response therapy.

DESCRIPTION OF THE FIGURES

FIG. 1B is a schematic of an arrangement for imaging ex vivo tissue samples in an automated platform.

FIGS. 2_1, 2_2 form a flowchart illustrating steps for imaging a multi-chamber slide.

FIG. 8 is a diagram of a desiccators apparatus for preparing a tissue sample for biodynamic imaging.

FIGS. 9A, 9B are diagrams of modifications to sample plates for improved imaging using aftermarket imaging retrofit devices.

FIG. 16 is a chart presenting three immobilization protocols and their relationship to a MSC characteristic metric.

DETAILED DESCRIPTION

Figure 1A:
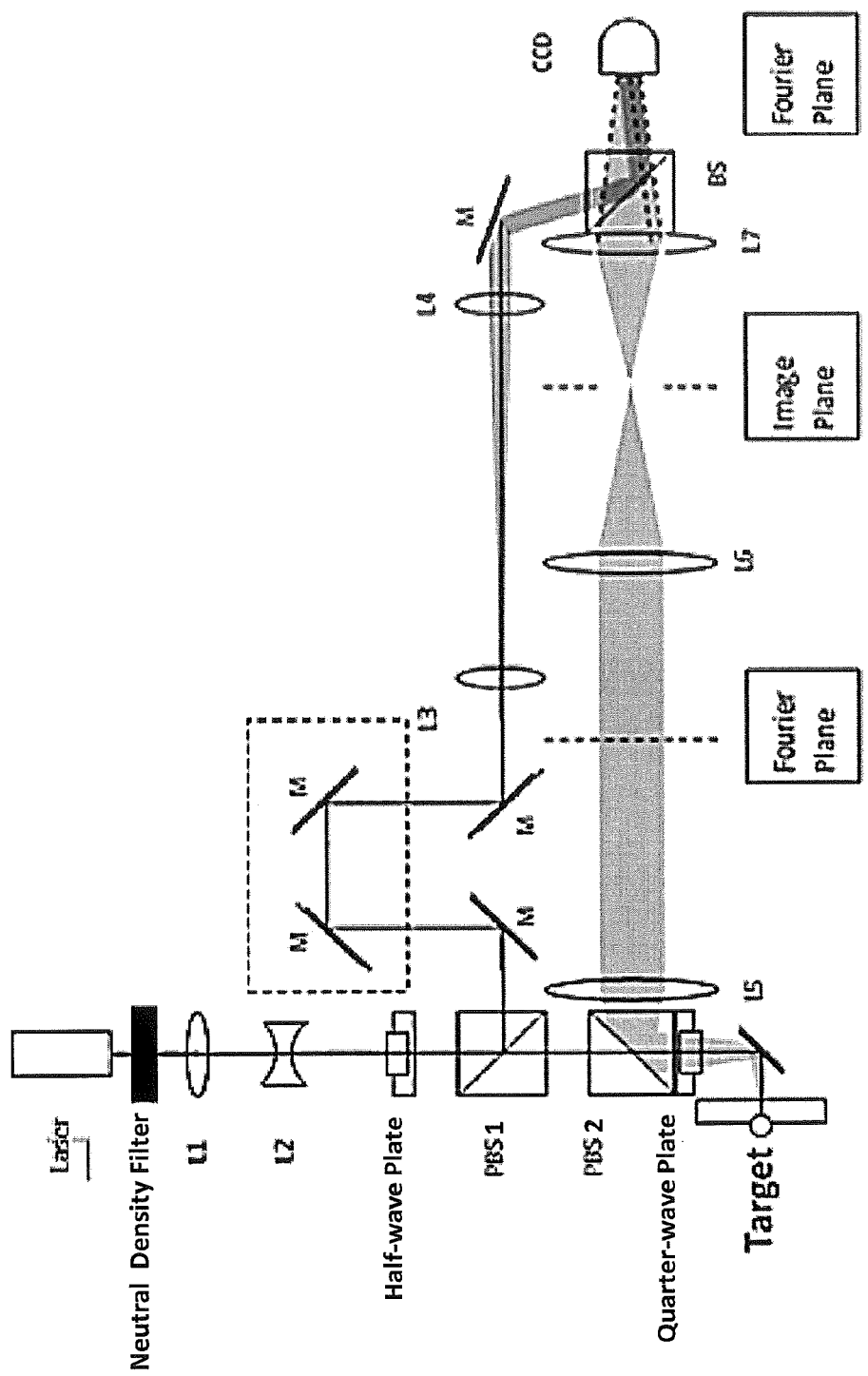
FIG. 1A is a schematic of an imaging system for use in the ex vivo imaging disclosed herein.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

A novel arrangement and method for ex vivo imaging is provided. Prior to discussing the arrangement and method of the present disclosure, reference is made to FIG. 1A to discuss imaging components further discussed in the present disclosure. Referring to FIG. 1A, The apparatus for holographic optical coherence imaging (OCI) is shown in FIG. 1A. There are two light paths in the optical coherence imaging system. The laser source provides light which is intensity-controlled by the neutral density filter and size-controlled by lenses L1 and L2. Light is communicated through a half-wave plate, and is then communicated through a polarizing beam splitter (PBS1) which generates an object path and a reference path. Lenses L3 and L4 expand the reference beam, and lens L5 performs the Fourier transform of the back-scattered dynamic speckle from a target. The wave plates (half-wave plate and quarter-wave plate) and the PBS2 ensure most of the laser power is in the object beam, and most of the back-scattered signal reaches the charge coupled device (CCD). The target is often a multicellular tumor spheroid, but can be any living biological specimen that is sufficiently immobilized, such as living tissue obtained by surgical biopsy or by needle biopsy. In TDS experiments, the images are captured at a fixed-depth (usually the mid-plane of the tumor tissue). For example, if the tumor spheroid has a diameter of 500 microns, the images captured by the CCD camera are the Fourier Domain back-scattered dynamic speckle holograms at the fixed depth of 250 microns in the tumor spheroid. Conversely, sections from multiple depths can be acquired to obtain stacks of images that are reconstructed into three-dimensional optical coherence volumetric images. In each 4 min interval, 2 acquisition rates are applied. First 200 images are captured at 25 fps; then another 100 images are captured at 0.5 fps. Thus after combining the high frequency data and the low frequency data together, in each 4 min interval (each data set), the spectrum frequency range is from 0.005 Hz to 12.5 Hz across more than 3 orders of magnitude.

The high-frequency acquisition generates a series of image frames in which the speckle varies in intensity from frame to frame. These intensities are analyzed using a Fourier transform to generate a high-frequency spectrum. The low-frequency acquisition similarly generates a low-frequency spectrum. These high- and low-frequency spectra overlap over a frequency range. A stitching algorithm is performed that combined the high- and low-frequency spectra into a single broad-band spectrum. This spectrum relates to the 300 images and constitutes one time-point spectrum. The process is repeated to generate a series of time-point spectra.

3D tissue constructs can be immobilized for tissue dynamics spectroscopy (biodynamic imaging) in a number of ways. The choice of stabilization protocol and stabilization plate that has been empirically determined for 3D specimens with variable characteristics (e.g., multicellular spheroids up to 2 mm in diameter). The immobilization protocol is determined via assessment of multiple parameters for each cell type and may be determined for these assays using the following formula:

> growth rate (1=slow, 3=moderate, 5=rapid)+growth as a loose cluster of cells (a reflection of the nature of cell-cell adhesions) (3) or growth as a tightly packed cluster (1) (a reflection of the nature of cell-cell adhesions)+detachment rate from culture flasks (a reflection of cell-extracellular matrix production(3=rapid, 1=slow)+size in millimeters (0.2,0.5,1,1.5,2).

This formula produces an MCS metric that ranges from 3.2 to 13. MCS grown are immobilized using one of the protocols A)-C) (FIG. 16) based upon the sum of individual growth characteristics.

3D tissue constructs that are not growing as multicellular spheroids may be immobilized by protocol C. These constructs include dense cell, suspension clusters, cell pellets, and layered or laminated cell pellets (more than one cell type or phenotype).

Tissue biopsies or other tissues removed from the body during surgery or autopsy can be immobilized for analysis an alternative protocol D) in which the tissue is minced into cubes in the range of 1-3 mm$^3$ while submerged in an appropriate transfer-holding fluid (balanced salt solution or tissue culture medium). Fluid is wicked away from the tissue pieces and they are transferred to the sample holder and adhered to the surface using 0.1-0.3 μL of sterile octyl/butyl cyanoacrylate topical tissue adhesive.

Most MCS or tissue may be analyzed using protocols A-D above. The protocols work well in situations where only a few changes to the growth medium are necessary to collect the TDS data. However, in accordance with one aspect of the present disclosure, plates are specifically provided for TDS where many fluid changes are desired (i.e., drugs, xenobiotics) or where the culture fluid is collected for procedures such as metabolomics analysis). Minimizing turbulence in the medium around the sample is desirable for repeated measurements where the culture fluid is exchanged. The plate shown in FIGS. 9A-9B modifies the standard 96-well plate specifically for TDS and may be used with protocols A-D above as needed. As shown in FIG. 9A, the MSC or tissue sample sits within a smaller well of variable diameter (1-4 mm) within the 96-well plate. The well diameter may vary according to the size of samples analyzed. The walls of the well are elevated so as to leave the sample submerged below the surface if the fluid is removed via the microchannel adjacent the well. Removing fluid from the entire well via the smaller microchannel well minimizes shear forces on the sample due to turbulence in the medium. Fluid can be added back to the well via the smaller microchannel well.

The arrangement shown in FIG. 1A can be used to analyze data from the target in various approaches, including biodynamic imaging (BDI) discussed in the U.S. patent application Ser. No. 14/526,247, filed on Oct. 28, 2014; Optical coherence imaging (OCI) discussed in U.S. Pat. No. 8,886, 295, issued on Nov. 11, 2014; and motility contrast imaging (MCI) discussed in U.S. patent application Ser. No. 13/704, 438, filed on Dec. 14, 2012, and Ser. No. 13/760,827, filed on Feb. 6, 2013, each of which is incorporated by reference into the present disclosure.

The target in FIG. 1A may be a single-well-based target or a multi-well target. Referring to FIG. 1B, a system is depicted to allow imaging of ex vivo samples in an automated platform. The arrangement depicted in FIG. 1B includes a computing device (e.g., a computer) coupled to two motorized actuators configured to receive signals from the computer and adjust horizontal and vertical (XY) positions of a sample holder. The sample holder is configured to receive a chamber slide with a plurality of wells, each configured to receive a biopsy sample for ex vivo imaging. The ex vivo sample is tissue excised from a subject tissue, such as a tumor spheroid. Multiple samples are obtained from the subject and placed in the multi-chamber slide for analysis.

The motorized actuators can include stepper motors that are configured to receive a digital signal from the computing device and cause movement of the sample holder, accordingly. It should be noted that the chamber slides include biopsies that are irregular in shape, therefore, not all parts of each well of the chamber slide can be analyzed since those parts may be void of the biopsy, or parts of a biopsy may be unsuitable for MCI/TDS imaging.

FIGS. 2_1 and 2_2 form a flowchart depicting the steps involved in a method for imaging a multi-chamber slide. The method includes several major steps, titled as: placing, determining boundaries, scanning_BDI, obtaining_OCI, obtaining_MCI, and checking NSD. These major steps are repeated for each chamber of the multi-chamber slides. The first major step, placing, includes inserting the multi-chamber slide containing the tumor biopsy into the sample holder. The step further includes refreshing growth medium in the chambers of the slide containing a tissue sample, and covering the chamber plate, e.g., using a cover glass slide. The step further includes waiting for the temperature of the multi-chamber to stabilize at 37° C.

The second major step, determining boundaries, includes moving the two motorized actuators to locate the corners of the biopsy in each chamber and recording the coordinates of the corners. The step further includes fixing the zero path depth for the imaging at 500 microns above the chamber slide bottom. The third major step, scanning BDI, includes scanning the biopsy sample and obtaining the full BDI data set (further described with reference to FIG. 3).

The fourth major step, obtaining OCI, refers to obtaining OCI intensity image data from the BDI data (further described with reference to FIG. 5). The fifth major step, obtaining_MCI, is for obtaining MCI data from the OCI data (further described with reference to FIG. 6). This fifth includes selecting the area of the tissue sample having the highest NSD and saving the coordinates of that area for further analysis.

These major steps are repeated for the second-through-fifth major steps for each chamber of the multi-chamber side until all the biopsies have been analyzed.

In reference to one embodiment of the present disclosure, a scan from each chamber containing a tissue sample of the multi-chamber slide is divided into a matrix of small rectangles. For example, each chamber (well) can be divided into 36 rectangles (see FIG. 4), and each rectangle can be divided into 500 time frames. Analyzing the 500 time frames leads to determining the best area of each biopsy for imaging.

Figure 3:
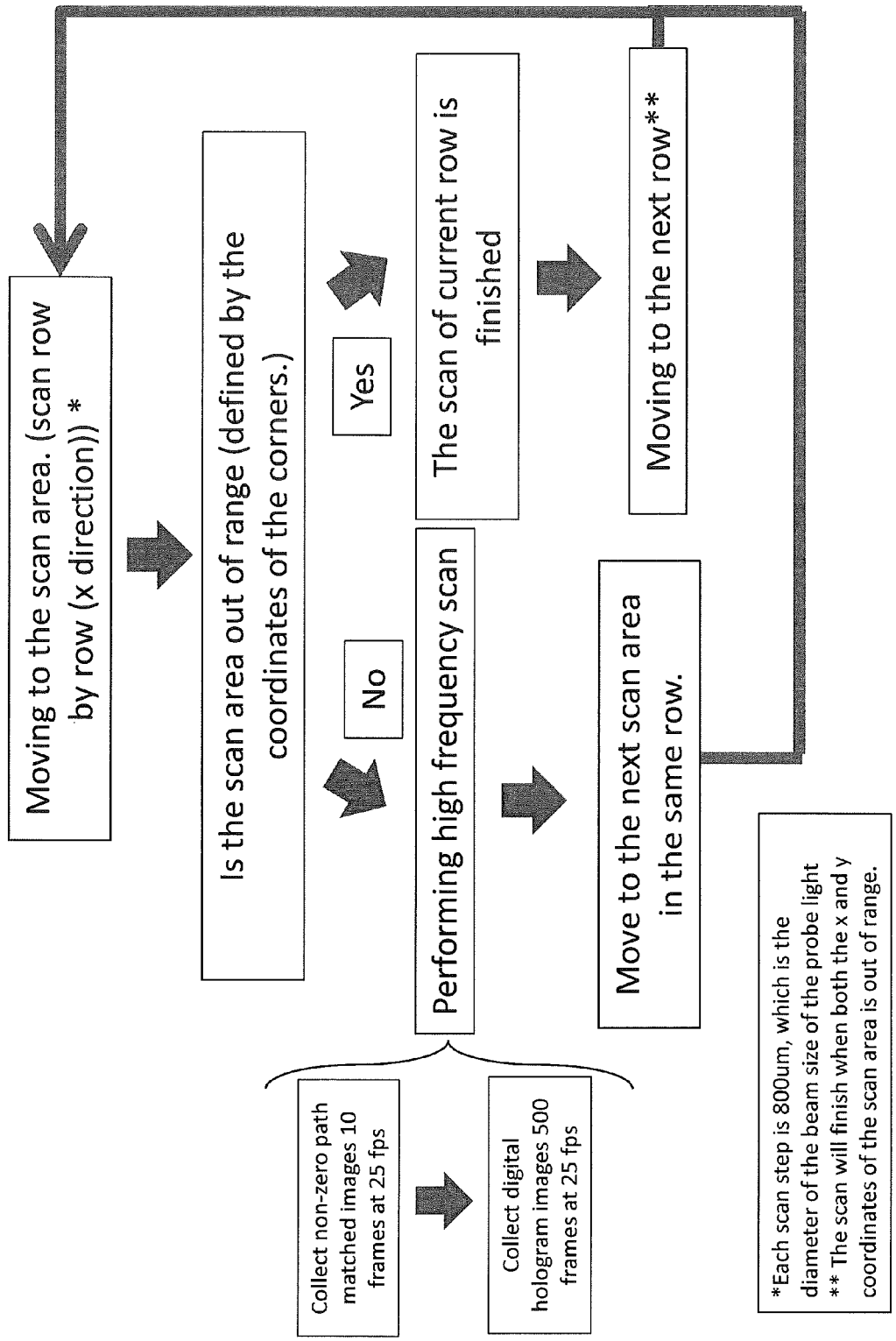
FIG. 3 is a detail flow chart of one step of the flowchart shown in FIGS. 2_1, 2_2.
Figure 4:
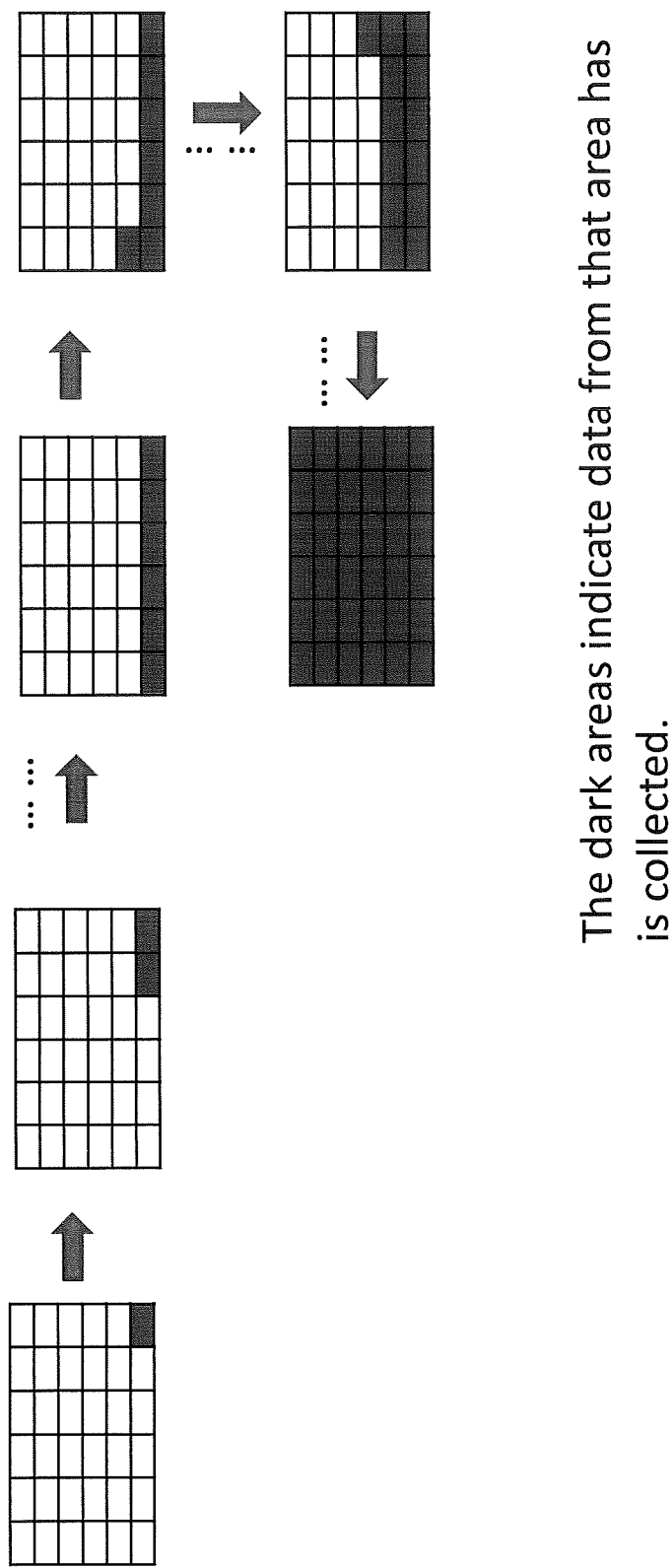
FIG. 4 is a representation of the scanning process effected by the steps of the flowchart in FIG. 3.

Referring to FIG. 3, the scanning_BDI step of FIG. 2_1 is further discussed. First, each row of rectangles of the chamber (e.g., 6 rows, as depicted in FIG. 4) is scanned before moving to another row. For each row as the scan data is being collected, the computing device of FIG. 1B determines if the scan area is still within the coordinates of the corners, which were identified in the determining boundaries step discussed in reference to FIG. 2_1. If it is determined that the scan area is outside of the boundaries, then the current row is deemed to be fully scanned and thus the computing device moves to the next row. If it is determined that the scan area is not outside of the boundaries, then a high-frequency scan is performed which includes collecting non-zero path-matched images at, e.g., 10 frames per second, followed by collecting digital images at, e.g., 500 frames at 25 frames per second. Thereafter, the computing devices moves to the next rectangle in the same row, before moving back to the top of the flow chart in FIG. 3.

An example of the rectangles for each row and rows in each chamber is shown in FIG. 4. The progression of scanning of the rectangles within each chamber is depicted by following the arrows. It can be appreciated that the scanning may follow a serpentine path from row to row.

Figure 5:
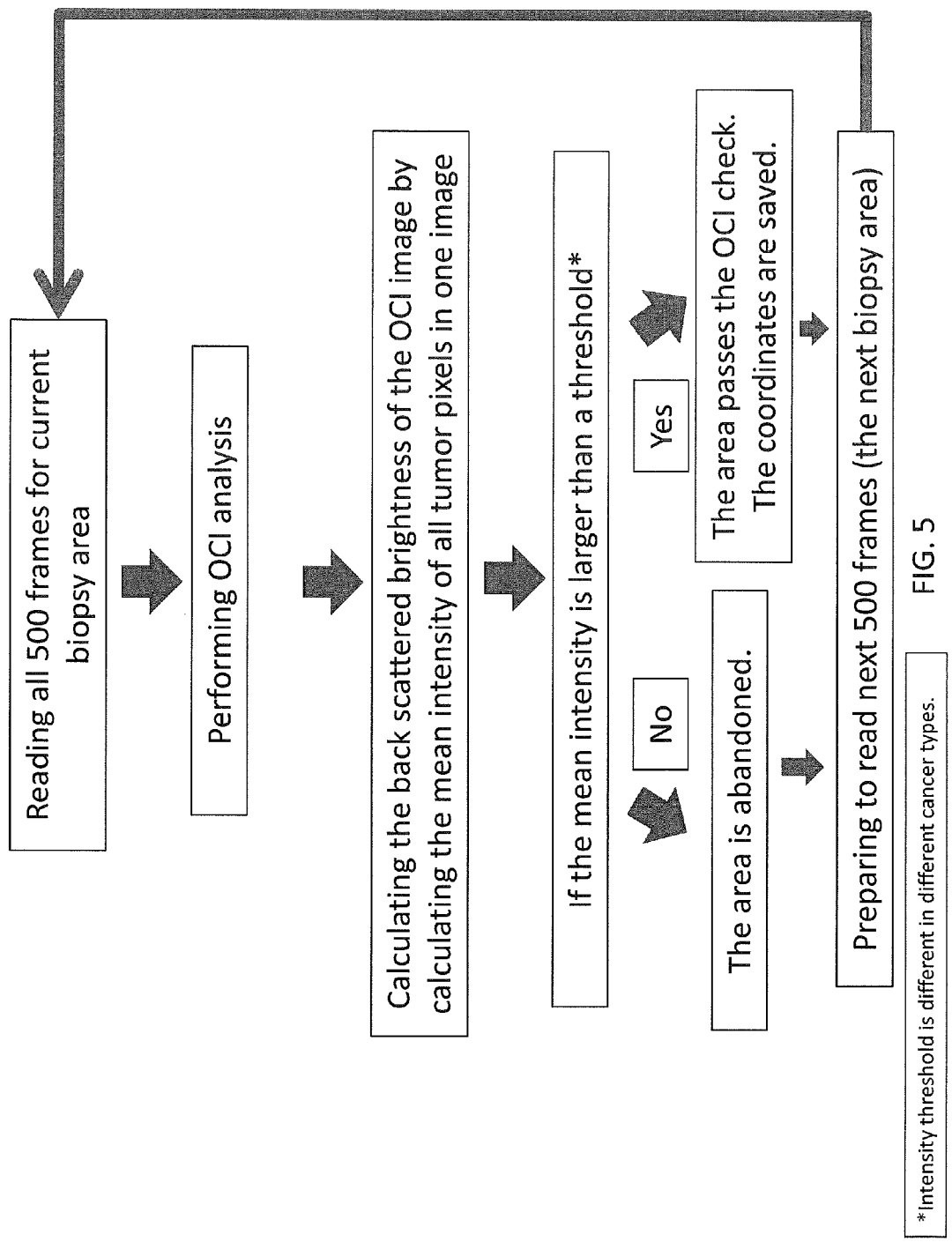
FIG. 5 is a detail flow chart of another step of the flowchart shown in FIGS. 2_1, 2_2.

Referring to FIG. 5, the obtaining_OCI, step discussed in FIG. 2_1, is discussed in more detail. The flowchart begins by reading data for all 500 time frames for each rectangle. Next OCI (optical coherence imaging) analysis is performed on all the data associated with each collection of 500 time frames. Next, the backscatter brightness associated with each OCI image constructed from all the frames from a rectangle is calculated by calculating the mean intensity of all tumor pixels in one image.

If the mean intensity is equal to or larger than a predetermined threshold (determined for the type of disease or type of tissue for which the biopsy was collected), the area is considered to have passed the OCI test, meaning that the image data is susceptible to OCI analysis. If the mean intensity is less than the predetermined threshold, the area is abandoned. The computing device then moves to analyze the next 500 frames associated with the next rectangle.

Figure 6:
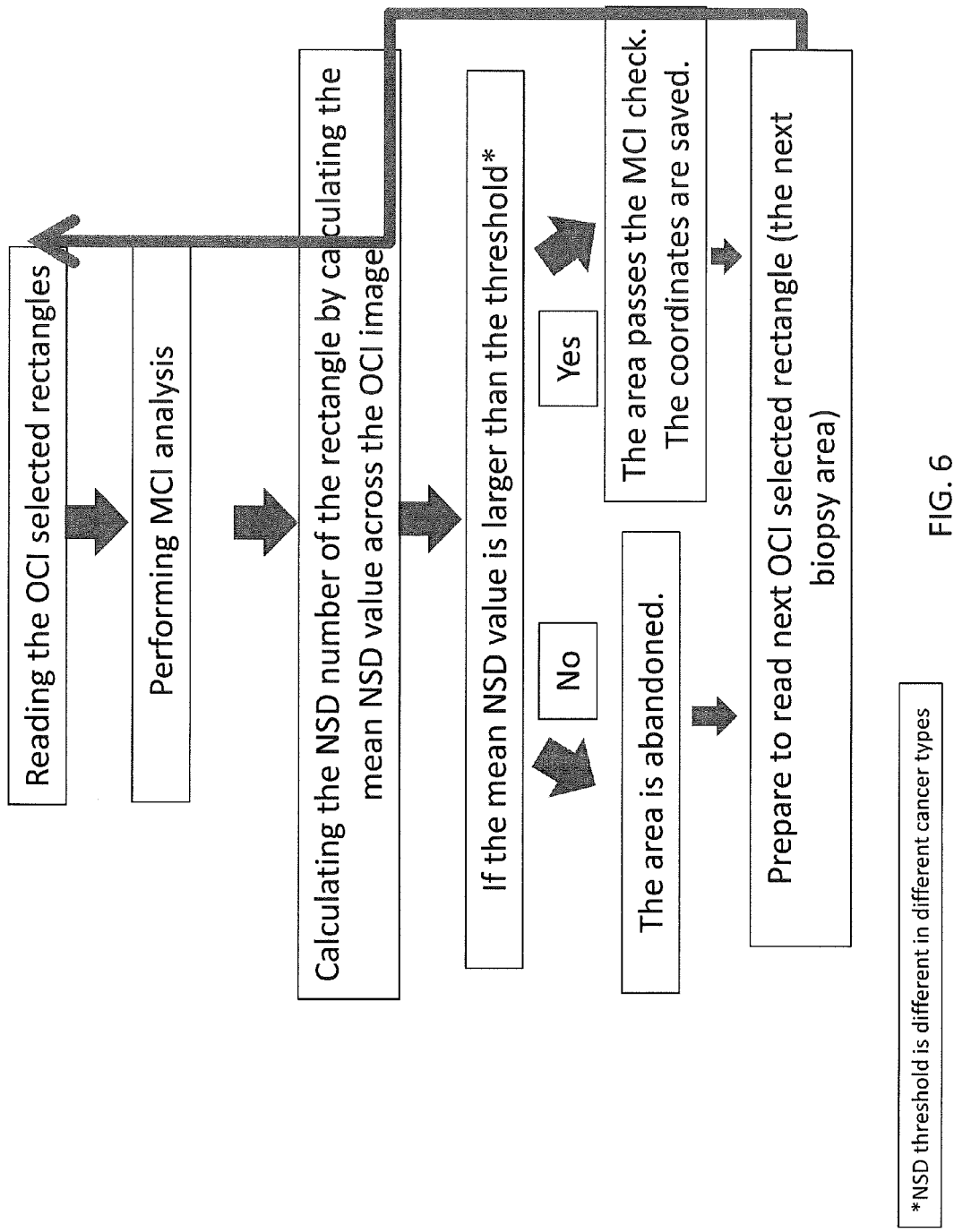
FIG. 6 is a detail flow chart of a further step of the flowchart shown in FIGS. 2_1, 2_2.

Referring to FIG. 6, the obtaining_MCI step and the checking NSD step, identified in FIG. 2_2, is further discussed. The computing device begins by analyzing the rectangles that passed the OCI criterion discussed in reference to FIG. 5; data from each OCI-passed rectangle is read. Next MCI (motility contrast imaging) analysis is performed on each OCI-passed rectangle. The normalized standard deviation (NSD) of each rectangle is obtained by calculating the mean intensity of all tumor pixels in one image composed of the 500 time frames If the mean NSD is equal to or larger than a predetermined threshold (determined for the type of disease and type of tissue for which the biopsy was collected), the area is considered to have passed the MCI test meaning that it is susceptible to MCI analysis, and thus the coordinates of the rectangle are saved for later imaging. The computing device then moves to analyze the next OCI-passed rectangle. If the mean NSD is less than the predetermined threshold, the area is abandoned. The computing device then moves to analyze the next OCI-passed rectangle.

As discussed in FIG. 2_2, once all the rectangles associated with one chamber are analyzed, the computing device can move to the next chamber. Alternatively, the computing device can move from the first chamber to the $n^{th}$ chamber and then back to the first chamber by analyzing rectangles associated with the same rows across all the chambers.

Figure 7:
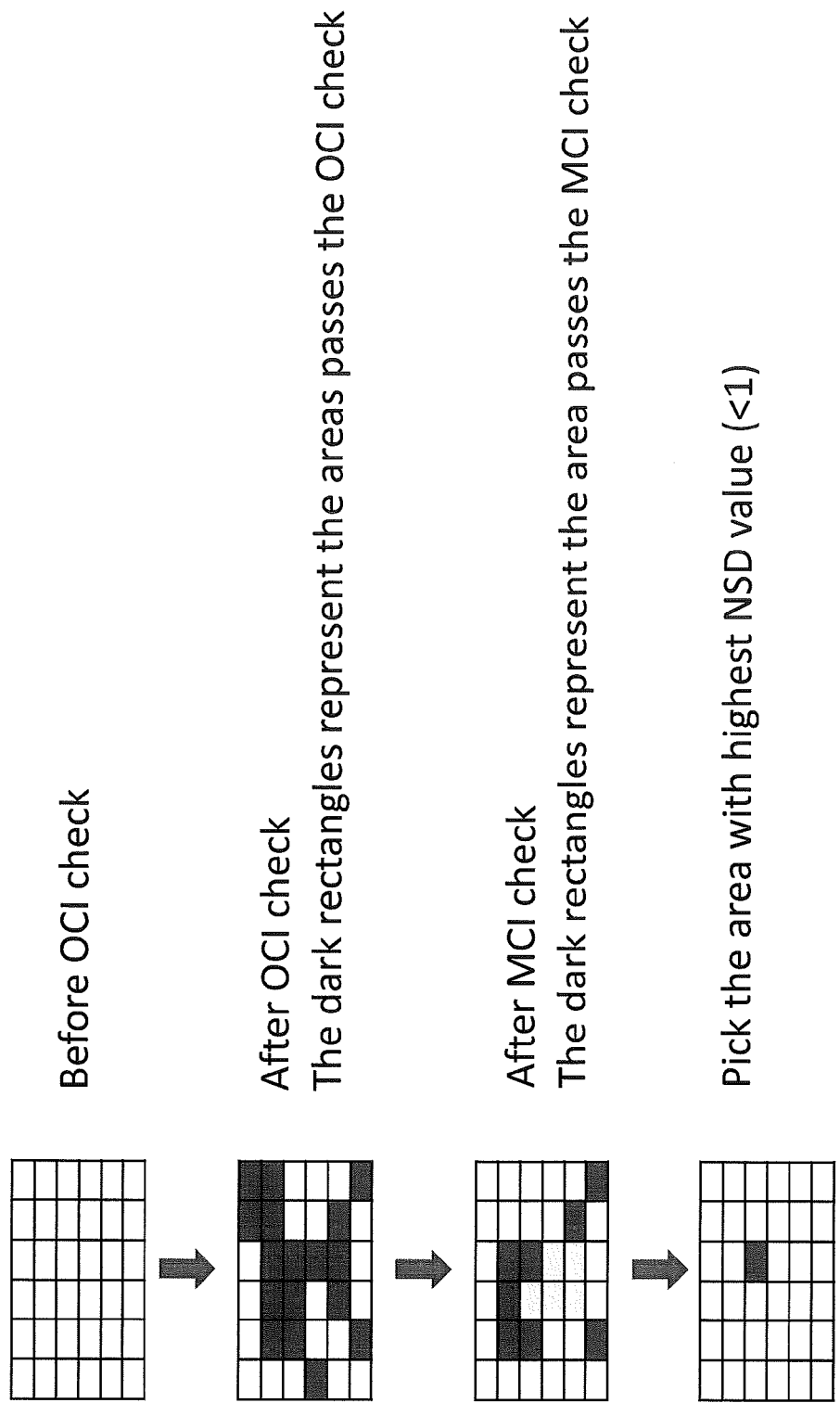
FIG. 7 is a representation of the selection of the imaged chambers according to the steps of the flowchart in FIG. 6

Referring to FIG. 7, analysis of each chamber is depicted. In particular, before OCI, all the rectangles in each chamber are considered. After the OCI analysis, a plurality of rectangles that have passed the OCI test, discussed in FIG. 5, are identified, as signified by the dark rectangles in the frame. After the MCI analysis, a plurality of rectangles that have passed the MCI test, discussed in FIG. 6, are identified, again signified as dark rectangles in the frame. As illustrated in FIG. 7, the OCI and MCI checks progressively pare down the chambers holding ex vivo tissue samples that can yield useful information using MCI.

Once the OCI and MCI checks have been completed, the computing device evaluates the NSD values for each of the remaining rectangles. The area with the highest NSD value is identified and is selected for full MCI imaging analysis. In other words, the previously described steps evaluates an ex vivo specimen to determine the area of the specimen that is the best candidate for MCI imaging and interrogation. The selected area is subjected to MCI imaging for 12-15 hours, with the first few hours (often four hours) used for baseline imaging. After the baseline imaging, the tissue sample is subjected to the perturbation or external influence, such as a particular drug, and the MCI imaging process is used to evaluate the impact of the external influence on the tissue, and particularly changes in cellular activity in response to the external influence. This process is repeated for the viable specimens in each chamber of the multi-chamber slide so that the excised tissue from the target tumor, for instance, can be subjected to multiple perturbations or external influences.

In one aspect of the disclosure, it is desirable to undertake specific steps in the preparation of irregular ex vivo tissue for biodynamic imaging in the steps of the flowchart of FIG. 2_1. In particular, the following steps may be followed to prepare a tumor biopsy for the initial "placing" steps in the flowchart. It is noted that the following steps are performed under sterile conditions in a laminar-flow biosafety hood:

1. Tissues removed by standard biopsy procedures or during surgery are placed in chilled (4° C.) growth medium (i.e., RPMI-1640 medium).
2. Tissues are placed in a 60 mm Petri dish and dissected into approximately 1 mm³ volumes using a surgical scalpel.
3. Perform stage-1 immobilization by picking up tissue pieces with micro-forceps and placing them in a sample container well (i.e., standard 96-well plate) to which has been added a small dot (0.1-0.5 μL) of sterile cyanoacrylate based adhesive that is suitable for surgical applications.
4. Perform stage 2 immobilization using a solution of 0.7-1% low-gel temperature (36° C.) agarose that has been melted by heating to 100° C. and then cooled to a few degrees above physiological temperature (38-40° C.). The agarose is dissolved in basal growth medium without any serum components (fetal calf serum).
5. With the sample on a thermoelectric warming plate at 38° C., layer the molten agarose onto the sample to cover to a depth of 1 mm. Seal the desiccator and exhaust the jar to 5-8 mm Hg with the vacuum pump. The set-up for this step is depicted in the diagram of FIG. 8. This step of degassing the sample is necessary for proper stabilization by removing any micro-bubbles or voids that remain around the sample and this level of vacuum does not harm the agarose enrobed tissue. After 3-5 minutes, turn off the vacuum pump, vent the desiccator and turn the temperature control down to 15-20° C. to cool the slide and rapidly gel the agarose. Once the agarose is gelled the sample may be removed.
6. After gelling of the agarose, overlay the sample with complete serum containing growth medium and mount in the BDI sample holder.

In certain respects, information obtained using the imaging techniques disclosed herein depends on the clarity of the image. Thus, for certain imaging instruments used to perform the BDI scanning steps described above, the specimen may require an offset from the optical axis to minimize reflection into the instrument. This is typically not a problem for dedicated BDI instruments that have the optics designed to minimize reflection. However, some aftermarket retrofits of existing microscopes may have optical paths that cannot be adjusted optimally for BDI. To address this problem and to increase the availability of BDI for a broad range of microscope customers, a custom solution compatible with existing microscope optics has been achieved using a modification of standard 96-well and 384-well (or more as the industry standard changes) assay plates. The 96-well or 384-well (or more) plates are designed with an angled bottom plate (angled up to six (6) degrees deflection), as depicted in FIGS. 9A-9B. The angled bottom does not allow reflected light from the assay plate to enter the MCI optics and thus reduces background noise and improves the signal-to-noise ratio for data acquisition. In addition, the 96-well plate may include a microchannel adjacent the angled bottom plate that allows for robotic fluid transfer and minimizes disruption of the sample during medium changes.

MCS may be grown in plastic culture dishes non-treated for tissue culture growth. The lack of treatment to the dish causes cells to adhere to each other rather than the plastic and small spheroids are formed. In a further modification of the assay plates described above, micro-scoring of non-tissue culture treated plastic can be used to grow spheroids that are also very adherent and immobilized and compatible with TDS. The defects in the surface allow the cells to attach and spheroids are formed along the length of the micro-score. The micro-score of the plate may be done using regular array patterns or matrices in 96-well plates or larger so that spheroids are formed in a manner compatible with systematic or non-biased sampling of individual samples for analysis.

In a further aspect of the present disclosure a closed-loop gradient-descent algorithm is provided that performs faithful sampling of statistically stationary regions of a fragmented biopsy sample without the need to sample the entire biopsy volume.

By way of background, tumor heterogeneity refers to different locations of a tumor having different properties. Tumor heterogeneity can relate to the local structure or the cellular constituents of the tumor, or it can relate to the genetic make-up of the tumor that may vary spatially across the tumor mass. Because of these differences, different parts of a tumor may respond in different ways to the same therapy. For instance, while the majority of a tumor may respond positively to a therapy, small regions that are spatially separated may not respond positively. Tumor heterogeneity is a key cause of cancer relapse and hence is a key concern for assays that assess or predict response to treatment. If a biopsy has a large size, it may be prohibitive to scan the entire mass, and hence a sampling approach is necessary in which a subset of the tumor is sampled by BDI to assess or predict response therapy.

One possible sampling approach is random sampling that would select regions from a tumor biopsy at random. This approach has the disadvantage that many of the selected sites may behave similarly, because the non-representative locations may have low probability of incidence.

Problems that involve a small number of samples that are used to estimate the properties of the sampled system fall under the topic of maximum likelihood methods that are closely related to maximum entropy methods. The goal is to have only a small number of measurements capture the variety, or heterogeneity, of sample responses. In conventional maximum likelihood approaches, a model is assumed with model parameters, and the small number of samples are used to optimize the parameter values. This parametric approach is not appropriate for tumor heterogeneity because there is usually no prior mathematical model that can describe the biopsy. In addition, if the non-representative regions have low probability of incidence, sampling can completely miss these regions.

The present disclosure contemplates a non-parametric maximum likelihood apparatus and method for identifying regions of a biological sample to be evaluated to assess or predict response therapy. This apparatus and method makes no assumptions about parametric values describing the drug response of a tumor biopsy. It is also suited to finding low-probability non-representative drug response regions in the biopsy. The disclosed method relies on a gradient descent in drug-response spectrogram space. Drug-response spectrograms are the primary data format of tissue dynamics spectroscopy. The drug-response spectrogram is a local property of the tissue and drug interaction. By creating a semi-local scalar field based on spectrograms from a limited area of the sample (the region of interest or ROI), a spatial gradient operator can be constructed that points in the direction of maximum ascent/descent. (Note: The ROI can be based on the diameter of the imaging device, CCD camera or microscope, so that each image obtained by the device has an ROI radius or diameter). The gradient information is fed back into the motion control system to step the imaging device by one ROI radius (or diameter) in the direction of the unit gradient vector. Another semi-local set of spectrograms is constructed at this new ROI, a new gradient vector is constructed, and the process is iterated. For every starting location on the sample, there are two unique trajectories that each ends on a local minimum and a local maximum, or else follows a saddle path.

Figure 10:
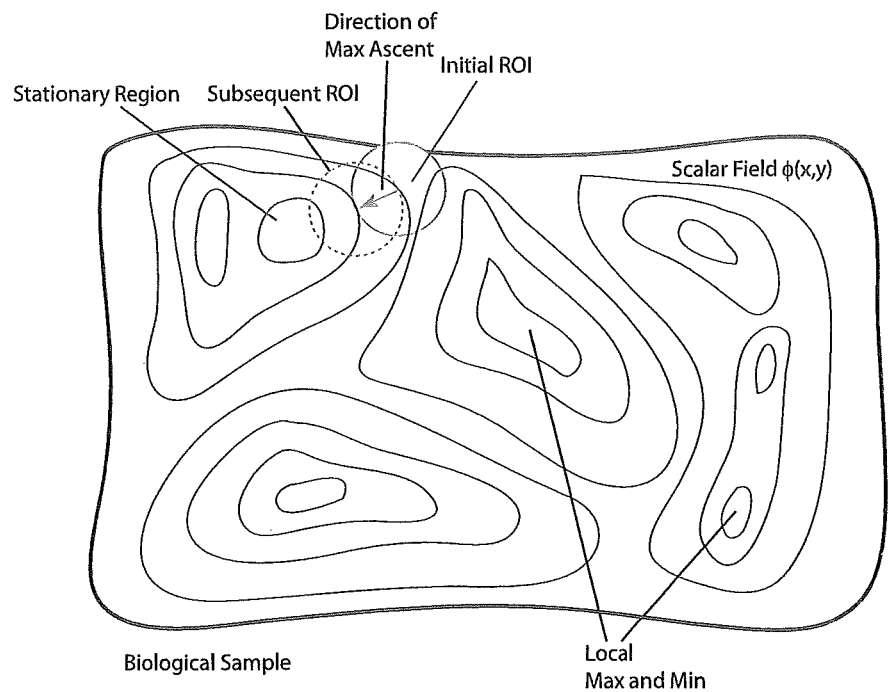
FIG. 10 is a representation of a biological sample with scalar fields and local minimums and maximums illustrating a method for optimizing regions of interest in the sample.

For example, a biological sample depicted in FIG. 10 is too large to measure completely. The imaging system probes a region of interest (ROI) around a selected point on the sample. Within this ROI a scalar field is constructed and the gradient operator is applied to it. This defines a vector pointed in the direction of greatest descent/ascent. The imaging device is then moved by one ROI radius (or diameter) in the direction of the unit vector to obtain a new ROI. The new ROI is then used, and the process iterates until a stationary region of the scalar field is reached—i.e., a region with essentially no descent/ascent vector. This stationary region is identified as the primary ROI for the particular biological sample from which to evaluate or predict the response of the overall biological sample to a particular stimuli or response therapy.

Figure 11:
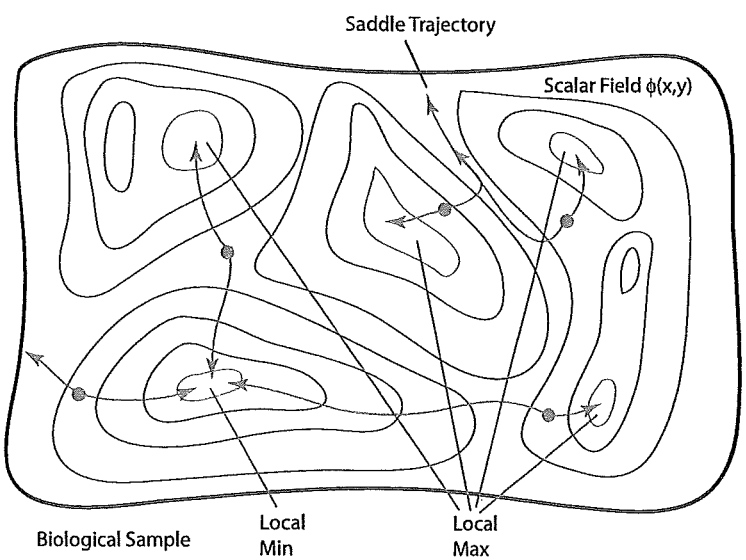
FIG. 11 is a representation of a biological sample with multiple paths for locating and optimizing regions of interest in the sample.

Several beginning locations and trajectories are shown in FIG. 11. The beginning locations are marked as the dots. Each dot has two trajectories emerging from it: one tracing a path of greatest descent into local minima, and the other tracing a path of greatest ascent to local maxima. These trajectories are the most efficient sampling paths that quickly zero in on the local minima and maxima without the need for exhaustive random sampling of the biological specimen. In FIG. 11, only five starting locations are needed for the paths to convergence on five out of seven of the maxima and minima in the biological sample. Note that some paths lead to saddle points rather than to a max or a min, but these saddle points also represent desirable sampling regions of the biological specimen because they represent a local mean-value response. Maxima, minima and saddles all share the property of maximum Lebesgue measure on the range of the scalar field and hence are the most representative of, and have the maximum likelihood of, a drug response associated with the specific feature captured by this scalar field.

The scalar field $\phi(x, y)$ used in the gradient descent/ascent method disclosed herein can be constructed as an inner product of the differential spectrogram with a target function defined on the time-frequency spectrogram plane. For instance, a target function $T_a(f, t)$ is defined in time-frequency and is multiplied by a drug-response TDS spectrogram $D(f, t; x,y)$ obtained at a location $(x, y)$ within the ROI on a tumor biopsy sample. The product is then summed or averaged over frequency and time to yield a scalar value at the location $(x, y)$ $$\phi(x,y) = \langle D(f,t;x,y) T_a(f,t) \rangle_{f,t}$$

Figure 12:
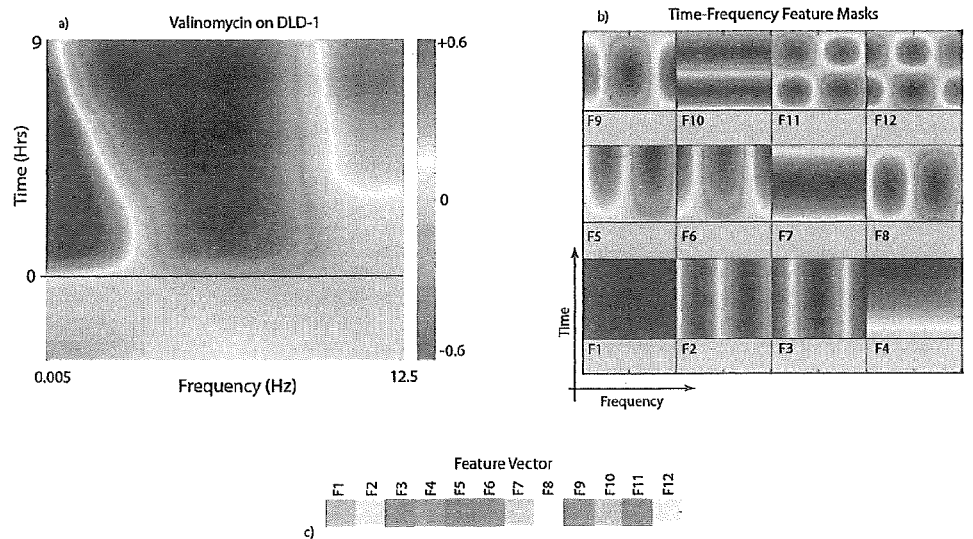
FIG. 12 is a drug response spectrogram for a DLD-1 tumor responding to a dose of valinomycin.

Many such scalar fields may be generated by using many different target functions. Examples of these target functions are shown in FIG. 12. On the left of the figure is an exemplary drug-response spectrogram of a DLD-1 tumor spheroid to an applied dose of valinomycin. The drug is applied at t=0, and the spectral response is monitored for nine hours. The resultant spectrogram is in the time-frequency domain, including a 4-hour baseline prior to the application of the drug. On the right of FIG. 12 are twelve feature masks $T_a(f,t)$. There are many ways of selecting sets of masks, and these can be chosen to extract specific biological functions, such as apoptosis as one example. Methods of generating and using feature masks are described in U.S. patent application Ser. No. 13/760,827, entitled "System and Method for Determining Modified States of Health of Living Tissue", filed on Feb. 6, 2013, the entire contents of which are incorporated herein by reference. In accordance with the methods of the present disclosure, the feature masks are used to generate a spatial scalar field $\phi_a(x,y)$ that can be operated on by the gradient operator to find the most representative regions in a heterogeneous biological sample.

The positions $(x, y)$ of the scalar field relate to the locations within the current ROI. The scalar field is operated upon by a gradient operator $$\vec{\nabla}\phi_a(x,y)$$

and the directions of steepest ascent/descent are given by $$\Delta \vec{r}_a = \pm \frac{\vec{\nabla}\phi_a(x, y)}{|\vec{\nabla}\phi_a(x, y)|}$$

Figure 13:
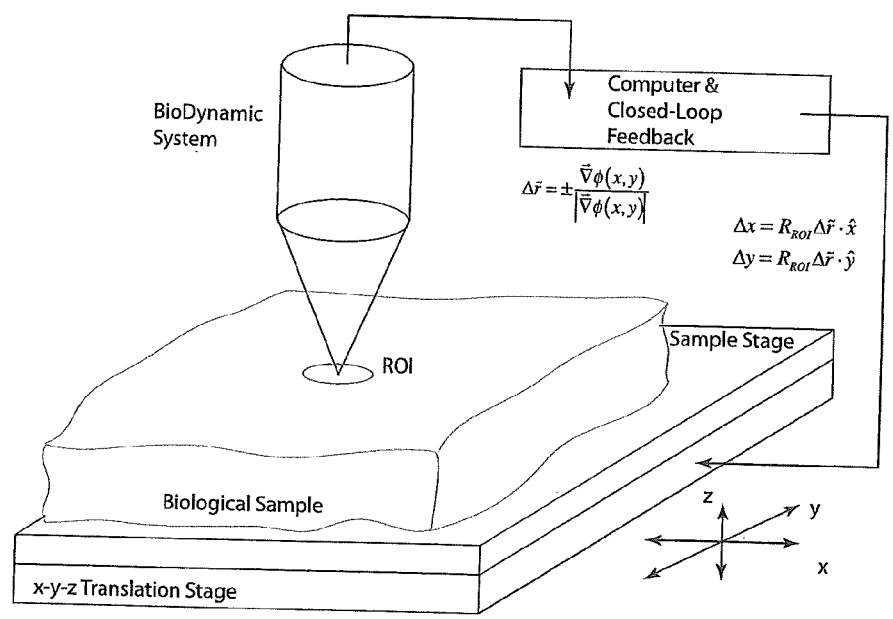
FIG. 13 is a schematic of a biodynamic system according to one aspect of the present disclosure.

In the system shown in FIG. 1B and FIG. 13, the computer can implement a feedback control algorithm to control the translation stages or motorized actuators to move the sample by the amount:

$$\Delta x = R_{ROI} \Delta \vec{r} \cdot \hat{x}$$

$$\Delta y = R_{ROI} \Delta \vec{r} \cdot \hat{y}$$

The trajectories shown in FIG. 11 have an optimized character that quickly finds the regions of stationary behavior that constitute the regions of highest Lebesgue measure on the range of the scalar field. In other words, these are the regions of maximum likelihood. These regions, defined within an interval (the separation between the contours), cover the majority of the heterogeneous specimen response to the applied therapy. Therefore, this approach of constructing feature masks on the time-frequency drug-response spectrogram to generate scalar fields, and operating on these scalar fields by the maximum gradient method, efficiently find the regions of maximum likelihood for the heterogeneous drug response of biological specimens.

The complete system is shown in FIG. 13 with the biodynamic system optics interrogating a region of interest (ROI) within which it captures differential drug-response spectrograms $D(f, t; x, y)$. This spectrogram is used to generate the displacement vectors (Dx, Dy) in the computer and close-loop feedback system to drive the translation stages in the directions of the greatest descent/ascent. This system also can be operated within three dimensions. The biodynamic imaging system is based on full-frame coherence gating that capture three-dimensional information inside tissue. Data stacks of differential drug-response spectrograms can be operated on by the three-dimensional gradient operator to give three dimensional displacements of greatest descent/ascent.

$$\Delta \vec{r} = \pm \frac{\vec{\nabla}\phi(x, y, z)}{|\vec{\nabla}\phi(x, y, z)|}$$

where the displacement vectors transmitted to the sample stage translation are $$\Delta x = R_{ROI} \Delta \vec{r} \cdot \hat{x}$$

$$\Delta x = R_{ROI} \Delta \vec{r} \cdot \hat{x}$$

$$\Delta x = R_{ROI} \Delta \vec{r} \cdot \hat{x}$$

The outcome of the heterogeneity sampling can be encapsulated in a small number of metrics that are communicated to the operator. According to the present disclosure, two combined metrics, identified herein as the "combined (Het, Div) metric", can be implemented: 1) Heterogeneity—or how spatially uniform is the response; and 2) Diversity—or phenotypic diversity corresponding to the difference in spectrogram features.

Figure 14:
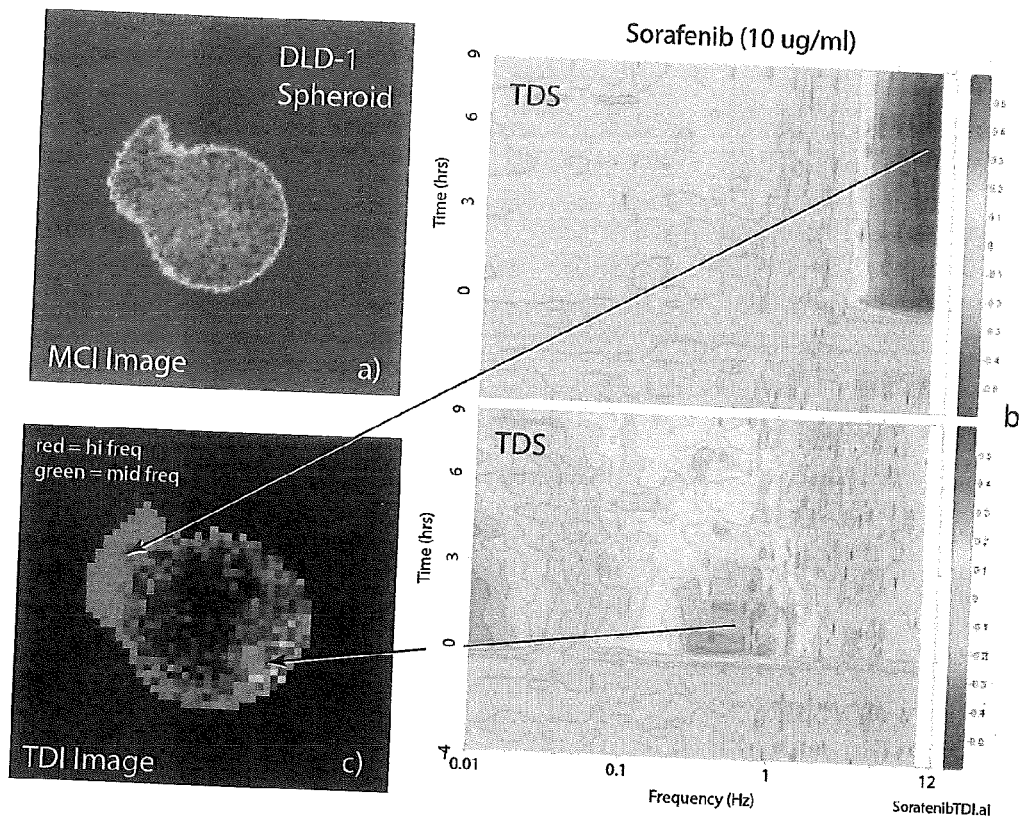
FIG. 14 are an MCI image, a spectroscopy image and a false color image of the DLD-1 tumor shown in FIG. 12.

An example of spatial non-uniformity is shown in FIG. 14 for the Raf inhibitor drug Sorafenib applied to a DLD-1 tumor spheroid. The motility contrast image in upper left of FIG. 14 is a simple metric that does not highlight the heterogeneous response of the sample to the applied drug. When the TDS analysis is applied across the pixels, relative differential spectrograms are obtained for positions (x, y). These spectrograms were analyzed for intensity and for spectral content. If the intensity of response was large, then the pixel is plotted in a bright color, and vice versa. In the image at the right of FIG. 14 the pixels are coded according to intensity and also according to spectral content. High spectral content is assigned the color red, and the mid-range frequency content is assigned the color green. Each pixel is then plotted as a red and green according to the spectral content (some pixels have both red and green and are perceived as yellow) as well as brightness to reflect the strength of the spectral components. The resulting false-colored image is shown in lower left of FIG. 14.

Figure 15:
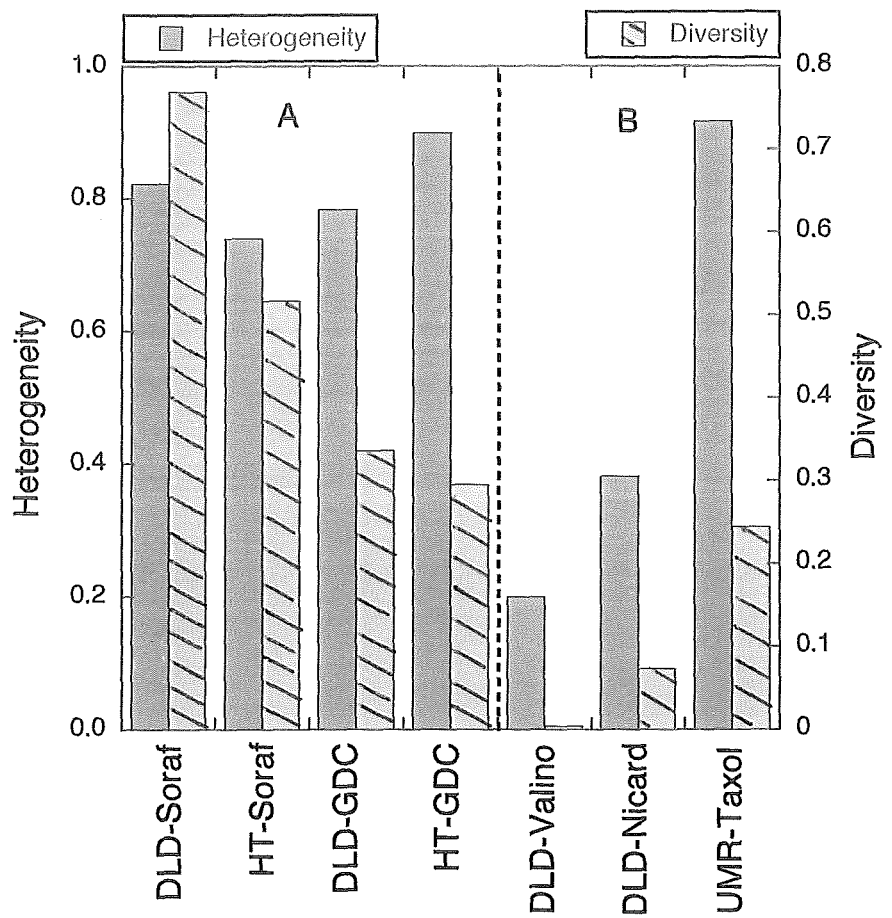
FIG. 15 is graph depicting combined (Het, Div) metrics for DLD-1 tumor shown in FIGS. 12, 14.

There are two types of heterogeneity observed in false-colored image in lower left of FIG. 14. There is spatial heterogeneity with the outer shell of cells displayed brightly, and the inner regions dark. The notable difference in spectral content contributes to the diversity of the drug response. Therefore, there are two measures that can be captured in a combined (Het, Div) metric. For the data in FIG. 14 the values are (Het, Div)=(0.83, 0.76). This shows both the high spatial heterogeneity as well as the high spectral diversity for DLD-1 responding to Sorafenib. This assay result would give a poor prognosis for this drug against this sample. This (Het, Div) metric was applied across several other drugs, with the results shown in FIG. 15. The Raf inhibitors all had high heterogeneity, while some (like Sorafenib) had high diversity, others (like GDC) had low diversity. One of the most uniform drugs was valinomycin. As another example, taxol affects the shell strongly, giving high spatial heterogeneity, but the spectral content appears the same for core and shell.

In this method, the region of interest is probed on a per-pixel basis and spectrograms are generated at each position (x, y). The spectrograms are then analyzed for metrics. Some metrics, like motility contrast in FIG. 20, are not highly specific. However, other metrics, like spectral content, can lead to large diversity values. When the (Het, Div) metric method is combined with the maximum likelihood sampling method, the operator of this system is provided quantitative values with which to make decisions on drug selection or on treatment.

Those skilled in the art will recognize that numerous modifications can be made to the specific implementations described above. The implementations should not be limited to the particular limitations described. Other implementations may be possible.

What is claimed is:

1. A method for ex vivo evaluation of biological sample response to a stimuli comprising:
   obtaining a sample of a target biological sample and placing the sample in a chamber of a sample holder;
   performing biodynamic imaging (BDI) on the sample to extract BDI data of the entire sample;
   generating optical coherence imaging (OCI) data from the BDI data;
   generating motility contrast imaging (MCI) data from the OCI data;
   using the MCI data, selecting an area of the sample having the highest normalized standard deviation (NSD) value;
   subjecting the sample to a perturbation or external condition; and
   performing MCI analysis on the selected area to determine the biological sample response to the perturbation or external condition.

2. The method of claim 1, wherein:
   the step of performing BDI on the sample includes obtaining 500 frames of digital hologram images of the sample; and
   the step of generating OCI data includes reading all 500 frames and performing OCI analysis.

3. The method of claim 2, wherein the step of generating OCI data includes:
   calculating a back-scattered brightness of the OCI image;
   determining a mean intensity in the image;
   abandoning the area of the sample in the image if the mean intensity is less than a threshold value.

4. The method of claim 1, wherein the step of generating MCI data includes:
   determining a mean NSD value for the image; and
   abandoning the area of the sample in the image if the mean NSD value is less than a threshold value.

5. The method of claim 1, wherein the step of performing BDI includes determining a boundary of the biological sample within the chamber whereby the BDI scan can be limited to the boundary of the biological sample.

6. A method for ex vivo evaluation of biological sample response to a stimuli comprising:
   obtaining a sample of a target biological sample and placing the sample in a chamber of a sample holder;
   using an imaging device to obtain a stimuli response spectrogram for the biological sample;
   generating semi-local scalar fields from spectrograms from a plurality of limited areas or regions of interest (ROI) of the biological sample;
   constructing a spatial gradient operator using the semi-local scalar fields of the plurality of ROIs;
   using the spatial gradient operator, identifying a direction of maximum ascent or descent from a current ROI, and generating a unit gradient vector corresponding to the direction;
   moving the biological sample relative to the imaging device by one ROI radius (or diameter) in the direction of the unit gradient vector;
   generating another semi-local set of spectrograms and a new gradient vector at a new ROI, and iterating this step until a stationary region of the scalar field is reached; and
   then identifying a then current ROI as the primary ROI for the biological sample to evaluate or predict the response to the overall biological sample to a particular stimuli or response therapy.

7. An apparatus for selective imaging of an ex vivo biological sample, comprising: a sample holder including a chamber for holding the biological sample;
   a biodynamic imaging system operable to extract biodynamic imaging data of the sample within the chamber of the sample holder;

a translation stage operable for at least relative x-y translation between the sample holder and the biodynamic imaging system;
a computer interface operably connected to the biodynamic imaging system and the translation stage, and configured to execute program instructions operable to:
perform motility contrast imaging and evaluation of the biological sample to generate a 3D spectrogram of the biological sample;
calculate a gradient in the spectrogram for the biological sample; and
activate the translation stage to iteratively translate the sample holder relative to the biodynamic imaging system to a plurality of regions of interest until a stationary point in the gradient is obtained.

* * * * *